United States Patent [19]

Ron et al.

[11] Patent Number: 5,597,897
[45] Date of Patent: Jan. 28, 1997

[54] PHARMACEUTICAL FORMULATIONS OF OSTEOGENIC PROTEINS

[75] Inventors: Eyal Ron, Lexington; Thomas J. Turek, Boston; Benjamin S. Isaacs; Himakshi Patel, both of Tewksbury; Richard A. Kenley, Andover, all of Mass.

[73] Assignee: Genetics Institute, Inc., Cambridge, Mass.

[21] Appl. No.: 81,378

[22] PCT Filed: Jun. 22, 1992

[86] PCT No.: PCT/US92/05309

§ 371 Date: Jun. 29, 1993

§ 102(e) Date: Jun. 29, 1993

[87] PCT Pub. No.: WO93/00050

PCT Pub. Date: Jan. 7, 1993

[51] Int. Cl.$^6$ .................................................... C07K 14/51
[52] U.S. Cl. ........................... 530/350; 530/399; 424/488
[58] Field of Search ...................... 514/12, 21; 530/399, 530/350; 424/488

[56] References Cited

U.S. PATENT DOCUMENTS

| | | | |
|---|---|---|---|
| 3,407,076 | 10/1968 | Ganz | 99/139 |
| 3,991,766 | 11/1976 | Schmitt et al. | 128/335.5 |
| 4,033,938 | 7/1977 | Augurt et al. | 260/78.3 R |
| 4,563,489 | 1/1986 | Urist | 524/21 |
| 4,637,931 | 1/1987 | Schmitz | 424/78 |
| 4,818,542 | 4/1989 | DeLuca et al. | 424/491 |
| 4,877,864 | 10/1989 | Wang et al. | 530/324 |
| 4,917,893 | 4/1990 | Okada | 424/423 |
| 4,933,182 | 6/1990 | Higashi et al. | 424/435 |
| 4,954,298 | 9/1990 | Yamamoto | 264/4.6 |
| 4,975,526 | 12/1990 | Kuberasampath | 530/350 |
| 5,053,485 | 10/1991 | Nieuwenhuis et al. | 528/354 |
| 5,108,753 | 4/1992 | Kuberasampath et al. | 424/422 |

FOREIGN PATENT DOCUMENTS

| | | |
|---|---|---|
| 2024196 | 12/1991 | Canada . |
| 140255 | 5/1985 | European Pat. Off. . |
| 0145240 | 6/1985 | European Pat. Off. . |
| 330180 | 8/1989 | European Pat. Off. . |
| 1332505 | 10/1973 | United Kingdom . |
| WO88/00205 | 1/1988 | WIPO . |
| 8909788 | 10/1989 | WIPO . |
| WO89/10409 | 11/1989 | WIPO . |
| 9009783 | 9/1990 | WIPO . |
| WO90/15586 | 12/1990 | WIPO . |
| 9200718 | 1/1992 | WIPO . |

OTHER PUBLICATIONS

Nelson, *Oral Surg.* 43: 836–843 (1977).
Miyamoto, Shimpei et al., *Clinical Orthopaedics and Related Research* 278: 274–285 (May 1992).
Jalil et al. *J. Microencapsulation*, 7(3), 297–325 (1990).
Ferguson et al., *Clin. Ortho. Rel. Res.* 219: 251–258 (1987).
Johnson et al *Clin. Orthop. Rel. Res.*, 230, 257–265 (1988).

*Primary Examiner*—Chhaya D. Sayala
*Attorney, Agent, or Firm*—Steven R. Lazar; Patricia A. McDaniels; Thomas J. DesRosier

[57] ABSTRACT

A composition comprising a pharmaceutically acceptable admixture of an osteogenic protein; a polymer matrix component selected from the group consisting of poly(lactic acid), poly(glycolic acid), and copolymers of lactic acid and glycolic acid; and an osteogenic protein-sequestering material.

26 Claims, No Drawings

PHARMACEUTICAL FORMULATIONS OF OSTEOGENIC PROTEINS

This application is filed under 35 U.S.C. 371 as a national phase application of PCT/US92/05309, as filed on Jun. 22, 1992, which claims priority from U.S. patent application Ser. No. 718,721, filed on Jun. 21, 1991, now abandoned.

BACKGROUND OF THE INVENTION

The subject invention relates to the field of osteogenic proteins and pharmaceutical -formulations thereof. More particularly, the subject invention involves pharmaceutical formulations designed to sequester osteogenic protein in-situ for a time sufficient to allow the protein to induce cartilage and/or bone formation.

Osteogenic proteins are those proteins capable of inducing, or assisting in the induction of cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. No. 4,877,864 and Wang et al. U.S. Pat. No. 5,013,549); a family of transforming growth factors (TGF-$\alpha$ and TGF-$\beta$) has been identified as potentially useful in the treatment of bone disease (See e.g. Derynck et al., EP 154,434); a protein designated Vgr-1 has been found to be expressed at high levels in osteogenic cells (see Lyons et al. (1989) Pro Natl. Acad. Sci. USA 86, 4554–4558); and proteins designated OP-1, COP-5 and COP-7 have purportedly shown bone inductive activity (see Oppermann, et al. U.S. Pat. No. 5,001,691).

Various attempts have been made at developing formulations designed to deliver osteogenic proteins to a site where induction of bone formation is desired. For example, certain polymeric matrices such as acrylic ester polymer (Urist, U.S. Pat. No. 4,526,909) and lactic acid polymer (Urist, U.S. Pat. No. 4,563,489) have been utilized, but these formulations do not sequester the osteogenic protein for a time sufficient to optimally induce bone formation and further have been found to erode too slowly for optimal bone formation.

A biodegradeable matrix of porous particles for delivery of an osteogenic protein designated as OP is disclosed in Kuberasampath, U.S. Pat. No. 5,108,753. While U.S. Pat. No. 5,108,753 discloses that a successful carrier for OP must bind the protein, act as a slow release delivery system, accommodate each step of the cellular response during bone development, and protect the protein from nonspecific proteolysis, no formulations are suggested which contain components that specifically sequester the OP at the site where bone formation is desired.

Okada et al., U.S. Pat. No. 4,652,441, U.S. Pat. No. 4,711,782, U.S. 4,917,893 and U.S. Pat. No. 5,061,492 and Yamamoto et al., U.S. Pat. No. 4,954,298 disclose a prolonged-release microcapsule comprising a polypeptide drug and a drug-retaining substance encapsulated in an inner aqueous layer surrounded by a polymer wall substance in an outer oil layer. Although bone morphogenic protein is listed as a polypeptide capable of such a formation, microencapsulation of osteogenic proteins prevents controlled release of such protein sufficient for optimal bone formation.

Collagen matrices have also been used as delivery vehicles for osteogenic proteins (see e.g. Jeffries, U.S. Pat. No. 4,394,370), but collagen frequently causes undesirable antigenic reactions in patients. Therefore, there remains a need for a pharmaceutical formulation capable of sequestering osteogenic proteins at a site where induction of bone formation is desired for a time sufficient to allow safe, effective induction of such bone formation.

SUMMARY OF THE INVENTION

In one embodiment, the subject invention provides a composition comprising a pharmaceutically acceptable admixture of an osteogenic protein; a polymer matrix component selected from the group consisting of poly(lactic acid), poly(glycolic acid), and copolymers of lactic acid and glycolic acid; and an osteogenic protein-sequestering alkylcellulose.

In another embodiment, the subject invention provides a composition comprising a pharmaceutically acceptable admixture of an osteogenic protein; a polymer matrix component selected from the group consisting of poly(lactic acid), poly(glycolic acid), and copolymers of lactic acid and glycolic acid; and an osteogenic protein-sequestering agent selected from the group consisting of hyaluronic acid, alginate, poly (ethylene glycol), polyoxyethylene oxide, carboxyvinyl polymer, and poly (vinyl alcohol).

In another embodiment, the subject invention provides a composition comprising polymeric particles having a spherical diameter of between about 150 and 850 microns and a porosity such that the surface area of the particles is between about 0.02 and 4 $m^2/g$, wherein the polymer is selected from the group consisting of poly(lactic acid), poly(glycolic acid), and copolymers of lactic acid and glycolic acid; optionally in admixture with osteogenic protein.

In yet another embodiment, the subject invention provides a composition comprising a pharmaceutically acceptable admixture of osteogenic protein and an effective solubilizing amount of a member selected from the group consisting of arginine, histidine, dextran sulfate, gamma-amino butyric acid, beta-amino propionic acid, glycine-glycine, glycine ethyl ester, histidine ethyl ester, lysine methyl ester, arginine methyl ester guanidine, sodium chloride, heparin, lysine, beta-alanine ethyl ester and agmatine.

DETAILED DESCRIPTION OF THE INVENTION

The osteogenic proteins useful in the practice of the subject invention are well known to those skilled in the art and include those discussed above. The preferred osteogenic proteins for use herein are those of the BMP family identified as BMP-1 through BMP-8 in U.S. Pat. No. 4,877,864; U.S. Pat. No. 5,013,649; WO 90/11366 published Oct. 4, 1990; and WO 91/18098 published Nov. 28, 1991. The most preferred is BMP-2, the mature protein sequence beginning with the amino acid Gln at nucleotide 1202 and ending with the amino acid Arg at nucleotide 1543, as described in detail in the '649 patent. Of course, combinations of two or more of such osteogenic proteins may be used, as may fragments of such proteins that also exhibit osteogenic activity and heterodimeric forms of such proteins. Recombinant proteins are preferred over naturally occurring isolated proteins. The amount of osteogenic protein useful herein is that amount effective to stimulate increased osteogenic activity of infiltrating progenitor cells, and will depend upon the size and nature of the defect being treated as discussed in more detail below, such amounts being orders of magnitude less than the amount of polymer matrix employed, preferably in the range of 1–50 µg of protein for each 10 mg of polymer matrix employed and more preferably in the range of 0.5–5 µg protein for each mg of polymer matrix employed.

The osteogenic proteins can be utilized in the form of a pharmaceutically acceptable solution or in lyophilized form. In either case it is optimal to stabilize and solubilize the osteogenic protein, preferably at concentrations of at least 1 mg/ml so that a pharmaceutically effective amount of protein can be delivered without undue volumes of carrier solution being necessary. However, a problem exists in that osteogenic proteins, particularly those of the BMP family have proven to be difficult to solubilize. As detailed in the examples below, it has been discovered that amino acids having a net positive charge (e.g. net 1+species such as arginine, histidine, lysine and the ethyl esters of glycine and beta-alanine), preferably a net 2+ charge (e.g. the ethyl ester of histidine, the methyl esters of lysine and arginine, and agmatine), are useful in this regard. Amino acids having a net zero charge are useful in this regard provided that the positive charge of the compound is sufficiently distant (at least 2–3 $CH_2$ units away) from the neutralizing negative charge (e.g. net neutral species such as gamma-amino butyric acid, beta-amino propionic acid and glycine-glycine dipeptide). Other solubilizing agents useful herein include dextran sulfate, guanidine, heparin and sodium chloride. For use in solubilizing BMP-2, the preferred solubilizing agents are arginine and histidine (including esters thereof). Arginine is used in concentrations of about 50–600 mM, preferably 300–500 mM. Histidine may be added to arginine to solubilize BMP-2, in concentrations of about 1–100 mM, preferably 10–50 mM. When histidine is used alone as a solubilizing agent, it is used in concentrations of about 50–600 mM, preferably 300–500 mM. Various well known methods may be used to compound the osteogenic protein and solubilizing agents for use herein, including but not limited to ultrafiltration, dialysis, gel filtration, and hydrophobic interaction chromatography.

The polymer matrix component useful in the practice of the subject invention is a polymeric material that can be formed into porous particles as described below thereby providing in-situ scaffolding for the osteogenic protein, while having biodegradable properties allowing for replacement by new bone growth. Examples are polymers of amino acids, orthoesters, anhydrides, propylene-co-fumarates, or a polymer of one or more α-hydroxy carboylic acid monomers, e.g. α-hydroxy acetic acid (glycolic acid) and/or α-hydroxy propionic acid (lactic acid). The latter can be employed in its d- or l- form, or as a racemic mixture, the racemic mixture being preferred. When a copolymer of lactic acid and glycolic acid is employed (PLGA), the molar ratio of monomers can range from 1:99 to 99:1 depending upon the desired bioerosion lifetime which in turn depends upon the clinical indication being addressed, as more than 50% of either monomer gives longer bioerosion lifetime (slower biodegradation). The molecular weight of the polymer can range from about 1,000 to 100,000 with 30,000–50,000 being preferred when a 50:50 copolymer is employed. The higher the molecular weight the slower the biodegradation.

The polymeric matrix component of the subject invention is used in the form of highly porous to hollow (with surface porosity) particles, hereinafter collectively referred to as "porous particles." These porous particles are generally spherical having diameters of 150 to 850 microns. This particle size creates sufficient spacing between particles to allow mammalian osteoprogenitor cells to infiltrate and be positively influenced by the osteogenic protein (evidenced by an increase in osteogenic activity/bone growth rate).

While it has generally been postulated ..that particles suitable as matrices for delivery of osteogenic proteins should be porous, the extent of porosity necessary-to optimally induce bone formation has not previously been studied. The present inventors have discovered that the average surface area per porous particle is critical to optimize bone formation. Specifically, porous particles useful in bone formation according to the present invention should have an average surface area of from about. 0.02 to 4 $m^2/g$. The present inventors have further discovered that it is possible to produce porous particles having the desired surface area by introducing a "porosigen" (composition capable of imparting porosity by increasing particle surface area) into the solution used to produce the porous particles. It is also possible to control the bioerosion rate by subjecting the porous particles to sterilizing doses of γ radiation. The higher the γ radiation dose, the faster the bioerosion.

The method of producing porous particles in accordance with the subject invention and discussed hereinbelow results in particles having a porosity such that the surface area of the particles is increased about 2–250 fold over the surface area of non-porous particles of comparable size. More specifically, e.g., non-porous PLGA particles having an average size of 400 µm have a surface area of 0.018 $m^2/g$. In contrast, PLGA particles useful in the subject invention made utilizing 50% NaCl as a porosigen have a surface area of between about 0.2 and 0.6 $m^2/g$; and particles made using sucrose as a porosigen have a surface area of between about 0.04 and 0.09 $m^2/g$ as described in Example 1. PLGA particles of the present invention made using liquid porosigen with homogenization as described in Example 2 have a surface area of between about 0.02 and 4 $m^2/g$.

A preferred method of production of the porous particles of the invention is, generally speaking, a solvent evaporation process comprising dissolving the polymer (in e.g. $CH_2Cl_2$), and adding a porosigen such as NaCl, mannitol or sucrose in solid and/or liquid form. When porosigen is added in solid form, the matrix-porosigen solution takes the form of a suspension. Another preferred method of production of the porous particles of the invention is a solvent extraction method, wherein the porosigen is added in liquid form with concomitant homogenization. When porosigen is added in liquid form with homogenization, the matrix-porosigen solution takes the form of an emulsion. With either method, the matrix-porosigen emulsion is added to an excess aqueous solution containing surfactant such as poly(vinyl alcohol) with controlled stirring and temperature. The resultant porous particles are hardened by extracting or evaporating residual solvent, and dried.

The porous nature of the particles of the present invention creates sufficient surface area for protein adsorption and increases biodegradation, the desirable extent of both being dependent upon the clinical indication being addressed. Surface area can be measured by any conventional technique. For example, BET surface area analysis can be employed using a Micromeritics ASAP 2000 system as is explained in more detail in Examples 1 and 2 below. The amount of porous particles used to treat a particular defect will, of course, depend upon the size of the defect being treated, and on the effective amount required to adsorb the osteogenic protein.

The osteogenic protein-sequestering material useful in the practice of the subject invention is a pharmaceutically acceptable material having a viscosity and polarity such that, when added to an osteogenic protein/porous particle combination, a malleable (putty-like) composite is formed that handles appropriately for surgical implantation into an injury site. Adding the sequestering agent to the combination of bioerodible porous particles plus osteogenic protein contains the adsorbed protein within the matrix for a time sufficient to allow the protein to increase the otherwise natural rate of osteogenic activity of the infiltrating mammalian progenitor cells. The sequestering material further allows the osteogenic protein to diffuse from the malleable composite over a time interval appropriate for optimally increasing the rate of osteogenic activity of the progenitor cells. In the absence of such a sequestering material, ostogenic protein desorbs from the PLGA particles in-situ at a rate such that the osteoinducing effect of the protein is not clinically significant.

A preferred family of sequestering agents is cellulosic materials such as alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, the most preferred being the cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the osteogenic protein from the polymer matrix and to provide appropriate handling of the composition, yet not so much that the progenitor cells are prevented from infiltrating the matrix, thereby providing the protein the opportunity to assist the osteogenic activity of the progenitor cells.

Additional optional components useful in the practice of the subject application include, e.g. cryogenic protectors such as mannitol, sucrose, lactose, glucose, or glycine (to protect the osteogenic protein from degradation during lyophilization), antimicrobial preservatives such as methyl and propyl parabens and benzyl alcohol; antioxidants such as EDTA, citrate and BHT (butylated hydroxytoluene); and surfactants such as poly(sorbates) and poly(oxyethylenes); etc.

According to the present invention, the osteogenic protein is not included in the PLGA polymerization solution or encapsulated in PLGA microcapsules but is added to the already polymerized porous particles. It is preferable to add the porous particles to the solution of osteogenic protein prior to addition of sequestering agent in order to allow the protein to adsorb onto the particles. Of course, the traditional preparation of formulations in pharmaceutically acceptable form ( i.e. pyrogen free, appropriate pH and isotonicity, sterility, etc.) is well within the skill in the art and is applicable to the formulations of the subject invention. The formulations may be provided to the clinic as a single vial formulation, either as a solution or in lyophilized form, or the formulation may be provided as a multicomponent kit wherein, e.g. the osteogenic protein is provided in one vial and the porous particles and sequestering agent are provided in a separate vial or vials.

As seen in Examples 4 and 5 below, the formulations of the subject invention provide malleable implants that allow therapeutically effective amounts of osteoinductive protein to be delivered to an injury site where cartilage and/or bone formation is desired. Such an implant may be used as a substitute for autologous bone graft in fresh and non-union fractures, spinal fusions, and bone defect repair in the orthopaedic field; in cranio/maxillofacial reconstructions,; for prosthesis integration, especially as a surface coating; in osteomyelitis for bone regeneration, and in the dental field for erosion of the alveolar ridge and periodontal disease. In certain of these uses, the compositions of the subject invention may be used in combination with various bone cements, including erodible bone cements such as poly(propylene-co-fumarate). The lower viscosity formulations may also be used as a percutaneous injection to accelerate healing of closed fractures. As alluded to above, the dosage regimen will be determined by the clinical indication being addressed, as well as by various patient variables (e.g. weight, age, sex) and clinical presentation (e.g. extent of injury, site of injury, etc.).

Currently, fresh autogeneic bone is widely used as a bone graft material. The limited supply of autogeneic bone, along with the necessity for an additional harvesting surgical procedure constitute major disadvantages in use of autogeneic bone for bone grafting. In accordance with the present invention, the porous particles of the invention may be added to autogeneic bone to extend the amount of material available for bone grafting. The porous particles may also be used in combination with a sequestering agent as a substitute for bone wax at the site of a bony injury to act as a bioerodible hemostat.

EXAMPLES

All components utilized in these examples are pharmaceutical grade. The polymeric particle component was made from a 50:50 (molar) random copolymer of lactic acid and glycolic acid (PLGA) having a weight average molecular weight of 30,000–50,000, a number average molecular weight of about 20,000 (by gel permeation chromatography relative to polystyrene standards), and an inherent viscosity of 0.35–0.45 dL/g. The osteogenic protein utilized was rBMP-2. The production and characterization of rBMP-2 is described in detail in the above-referenced U.S. Pat. No. 5,013,649. The sequestering agents utilized included carboxymethyl-cellulose, hydroxy-propylmethyl cellulose, sodium alginate, hyaluronic acid, and poly(ethylene glycol). The carboxylthylcellulose (CMC) utilized contained 0.7 degree of substitution (carboxymethyl groups per hydroxy group on cellulose and had a viscosity of 2480 cps.

EXAMPLE 1—PREPARATION OF POROUS PARTICLES BY SOLVENT EVAPORATION TECHNIQUE

PLGA was dissolved in $CH_2Cl_2$ (15% w/v), and 10 g porosigen (7.5% w/v) was suspended in this solution. The resulting solution was added to an excess poly(vinyl alcohol) aqueous solution (0.1% w/v). After a few hours of stirring under partial vacuum (24 inches Hg), the particles were hardened in excess cold ethanol (95%). The resulting particles were washed with water for injection and vacuum dried to give a free-flowing product. BET surface area analysis was performed using a Micrometrics ASAP 2000 system. The measurement of surface area is based upon adsorption and desorption of Krypton gas at the surface and within the pores of the solid sample. The unit calculates and prints out the surface area:

$$\frac{1}{VA[(P_0/P) - 1]} = \frac{C-1}{V_m C} (P/P_0) + \frac{1}{V_m C}$$

$V$ = volume absorb at pressure $P$  
$P/P_0$ = relative pressure  
$C$ = constant  
$V_m$ = Monolayer Capacity $P_0$ = saturation pressure  
$P$ = pressure  
$A$ = gas cross sectional area -continued By plotting $\frac{1}{VA((P_0/P)-1)}$ vs $P/P_0$, the slope being $\frac{C-1}{V_mC}$ and the intercept being $\frac{1}{V_mC}$, the surface area $S_t = \frac{V_m NA}{V}$ where $N$ = Avogadro's number and $V$ = molar volume.

Reactant details and results are depicted in Table 1 and Table 2, respectively.

TABLE 1

| Batch No. | PLGA (grams) | CH2CL2 (mL) | Porosigen (type/%) | PVA (mL) | Impellers (top/btm) | Stirring (rpm) |
|---|---|---|---|---|---|---|
| 1 | 10 | 67 | NaCl/50 | 1200 | (2rshtn/A-100) | 215 |
| 2 | 10 | 67 | NaCl/80 | 1200 | (2rshtn/A-100) | 215 |
| 3 | 6.7 | 67 | suc/50 | 1200 | (2rshtn/A-100) | 215 |
| 4 | 6.7 | 67 | NaCl/50 | 1200 | (2rshtn/A-100) | 235 |
| 5 | 16 | 106 | suc/50 | 2000 | (A-310/A-310) | 140 |
| 6 | 20 | 133 | suc/50 | 2000 | (A-310/A310) | 140 |
| 7 | 20 | 133 | suc/50 | 2000 | (A-310/A-310) | 140 |
| 8 | 20 | 133 | suc/50 | 2000 | (8.5rsh/A-310) | 100 |
| 9 | 20 | 133 | suc/50 | 2000 | (8.5rsh/A-310) | 140 |
| 10 | 20 | 133 | suc/50 | 2000 | (2rshtn/A-100) | 140 |

TABLE 2

| Batch No. | Mn | Mw | Dp | Surface Area (m²/g) | Yield % 250–710 μm | Density (gms/cc) |
|---|---|---|---|---|---|---|
| 1 | 17500 | 30800 | 1.75 | 0.54 | 27.3 | 0.41 |
| 2 | 19400 | 31700 | 1.64 | 0.037 | 71.6 | 0.67 |
| 3 | 19700 | 40900 | 2.07 | 0.089 | 92.7 | 0.70 |
| 4 | 20300 | 37700 | 1.86 | 0.28 | 69.5 | 0.37 |
| 5 | 20400 | 32600 | 1.60 | 0.035 | N/A | N/A |
| 6 | 20200 | 37700 | 1.86 | 0.079 | 79.5 | 0.64 |
| 7 | | | | 0.060 | 85 | 0.76 |
| 8 | | | | 0.038 | 85 | 0.86 |
| 9 | | | | 0.057 | 65 | 0.71 |
| 10 | 20200 | 37700 | 1.86 | 0.060 | 64 | 0.68 |

EXAMPLE 2—PREPARATION OF POROUS PARTICLES BY SOLVENT EXTRACTION TECHNIQUE

A 100-g sample of PLGA was dissolved in 670 mL of CH₂Cl₂. The porosigen solution was prepared by dissolving 5 g NaCl in 50 mL of a 0.2% aqueous solution of poly(vinyl alcohol). A 50-mL aliquot of the porosigen solution was added to a homogenizer and agitated at 3300 rpm. The PLGA solution was then added to the homogenizer (with agitation)- A 77 mM NaCl sdlution in 10 liter of 0.2% aqueous poly(vinyl alcohol) was added to a 12-liter reactor and agitated at 175 rpm. The PLGA/porosigen suspension was added to the reactor over 90 minutes. A 77 mM NaCl solution in 0.2% aqueous poly(vinyl alcohol) was then pumped into and out of the 12-liter reactor, thereby extracting methylene chloride from the mixture. After solvent extraction was complete, agitation was stopped, the porous particles are allowed to settle, the supernatant was decanted, and the particles were hardened with ethanol (95%) followed by washing with water or a solution of polysorbate 20 (0.05%) in water. The washed particles were dried by vacuum or convection techniques. Particles prepared according to this procedure typically have 0.09 g/cc bulk density, and total surface area=4 m²/g. The dried particles can be sterilized by ethylene oxide exposure or γ irradiation. As noted above, the γ radiation dose influences bioerosion rate. Table 3 gives examples of porous particles prepared by the above process.

TABLE 3

| Batch No. | Homogenizer (rpm) | Porosigen Soln, (mL) | Density (g/cc) | Yield % 150–500 μm |
|---|---|---|---|---|
| 1 | 10,000 | 50 | 0.09 | 80 |
| 2 | 3,500 | 50 | 0.15 | 80 |
| 3 | 6,000 | 50 | 0.09 | 95 |
| 4 | 3,000 | 50 | 0.10 | 95 |
| 5 | 1,900 | 50 | 0.29 | 90 |
| 6 | 2,200 | 50 | 0.10 | 95 |
| 7 | 2,000 | 50 | 0.09 | 99 |
| 8 | 2,000 | 25 | 0.14 | 90 |
| 9 | 2,000 | 12.5 | 0.24 | 90 |
| 10 | 2,000 | 20 | 0.28 | <75 |
| 11 | 2,000 | 20 | 0.18 | >75 |
| 12 | 2,000 | 17.5 | 0.16 | 95 |
| 13 | 2,000 | 15.5 | 0.21 | 94 |
| 14 | 2,500 | 15.5 | 0.17 | 90 |
| 15 | 2,200 | 15.5 | 0.19 | 90 |

EXAMPLE 3—SOLUBILIZATION OF PROTEIN

Solubility of rBMP-2 in the excipients listed in Table 4 below was determined by dialysis in accordance with the following. Concentrations were determined by absorbencies at 280 nm using an extinction coefficient of 1.62. Protein solution (1 ml) containing 2–3 mg/ml of protein, 0.5M arginine and 10 mM phosphate (pH 6.5) was dialyzed against 1000 ml of buffer containing 0.5M excipient of choice (see Table 3) and 0.5M arginine, pH 6.5. The dialysis was carried out at room temperature. The excipients were allowed to equilibrate with the protein solution. The protein solution was then dialyzed twice against 1000 ml of an arginine-less buffer solution of otherwise identical composition. Solubility results are presented in Table 4. Unless otherwise indicated, excipients were tested at standard concentrations of 500 mM.

TABLE 4

| EXCIPIENT | NET CHARGE (at neutral pH) | SOLUBILITY (mg/ml) |
|---|---|---|
| ε-amino caproic acid | 0 | <0.4 |
| δ-amino valeric acid | 0 | <0.4 |
| γ-amino butyric acid | 0 | ≥1.7 |
| β-amino propionic acid | 0 | ≥1.1 |
| Glycine-Glycine dipeptide | 0 | ≥1.8 |
| Glycine | 0 | ≤0.4 |
| Arginine | 1+ | ≥5.4 |
| Lysine | 1+ | ≥0.9 |
| Guanidine | 1+ | ≥1.8 |
| Glycine (ethyl ester) | 1+ | ≥2.2 |
| Histidine (ethyl ester) | 2+ | ≥2.2 |
| Lysine (methyl ester) | 2+ | ≥2.2 |
| Arginine (methyl ester) | 2+ | ≥2.2 |
| Histidine | 1+ | ≥2.2 |
| Dextran sulfate | | ≥1.7 |
| 1.0M NaCl | 0 | ≥1.8 |

EXAMPLE 4 — IMPLANT ANALYSIS rBMP-2 (22 μg), mannitol (8 mg), and epsilon aminocaproic acid (2M, 20 μl) were lyophilized onto the PLGA particles (10 mg, 20% porosity, 325 mm). CMC (5.5 mg, ~9%) was added and the solid powder was sterilized using ethylene oxide.. Water for Injection (60 μl) was added to form a malleable implant of the composite. As a control, the same formulation was made without the CMC, in which case a gelatin capsule was used to hold the formulation in place. Both formulations were implanted in a 5 mm rat femur defect. The rats were sacrificed after twelve weeks. Ex-vivo analysis of the new bone was performed radiographically relative to the contralateral femur. Surprisingly, 83% (10 of 12) of the femur defects showed union utilizing the formulations of the subject invention, compared with only 50% (4 of 8) for the control.

EXAMPLE 5 — IMPLANT ANALYSIS

A 300-μL aliquot of 0.12 mg/mL rBMP2 solution (in 0.25M arginine, 10 mM histidine, pH 6.5, plus 20 mM calcium chloride) was added to 9.6 mg of porous particles (0.16 g/cc density, surface area=approximately 0.8 m²/g, sterilized by 2.5 Mrad γ radiation). To this mixture was added 15 mg sodium alginate. Gentle mixing provided a malleable composite. Similar formulations were made using 9 mg of hydroxypropylmethylcellulose or 9 mg carboxymethylcellulose except that the 0.12 mg/mL rBMP2 was solubilized in 0.25M arginine plus 10 mM histidine, pH 6.5 (no added calcium chloride). As controls, malleable formulations were prepared with 0.25M arginine plus 10 mM histidine containing 0 mg/mL rBMP2. The formulations were implanted into 8 mm diameter critical size circular defects in rat calvarium. After 21 days the animals were sacrificed and bone regeneration assessed by radiomorphometry (X-O MATL high contrast x-ray film, using Cambridge 520 Image Analysis System). The control samples for alginate, CMC, and hydroxypropylmethyl-cellulose formulations, respectively, showed only 18%, 10% and 10%, radiopacity. By comparison the alginate, CMC and hydroxypropylmethylcellulose formulations (with added rBMP2) showed, respectively, 72%, 70% and 67% radiopacity indicating significant new bone growth.

What is claimed is:

1. A composition comprising a pharmaceutically acceptable admixture of
   (i) an osteogenic protein;
   (ii) a polymer matrix component selected from the group consisting of poly(lactic acid), poly(glycolic acid), and copolymers of lactic acid and glycolic acid; and
   (iii) an osteogenic protein-sequestering alkylcellulose, wherein said alkylcellulose is present in an amount of approximately 0.5–20 wt % based on total composition weight, wherein said osteogenic protein is not encapsulated within the polymer matrix.

2. The composition of claim 1 wherein the osteogenic protein is selected from the group consisting of the members of the BMP-family.

3. The composition of claim 2 wherein the osteogenic protein is BMP-2.

4. The composition of claim 2 wherein the cellulosic material is selected from hydroxypropylmethylcellulose and carboxymethylcellulose.

5. The composition of claim 3 wherein the cellulosic material is selected from hydroxypropylmethylcellulose and carboxymethylcellulose.

6. The composition of claim 5, wherein the polymer matrix component is a copolymer of lactic acid and glycolic acid.

7. A composition comprising a pharmaceutically acceptable admixture of
   (i) BMP-2;
   (ii) a polymeric matrix component comprising polymeric particles having a diameter of between about 150 and 850 microns and a porosity such that the surface area of the particles is between about 0.02 and 4 m²/g, wherein the polymer is selected from the group consisting of poly(lactic acid), poly(glycolic acid), and copolymers of lactic acid and glycolic acid; and
   (iii) a protein sequestering amount of carboxymethylcellulose, wherein said carboxymethylcellulose is present in an amount of approximately 0.5–20 wt % based on total composition weight, wherein said BMP-2 is not encapsulated within the polymeric matrix.

8. The composition of claim 1 wherein the osteogenic protein is TGF-β.

9. The composition of claim 1 wherein the osteogenic protein is Vgr-1.

10. The composition of claim 1 wherein the osteogenic protein is OP-1.

11. The composition of claim 1 wherein the osteogenic protein is selected from COP-5 and COP-7.

12. A composition consisting essentially of a pharmaceutically acceptable admixture of
   (i) an osteogenic protein;
   (ii) a polymer matrix component selected from the group consisting of poly(lactic acid), poly(glycolic acid), and copolymers of lactic acid and glycolic acid; and
   (iii) an osteogenic protein-sequestering alkylcellulose.

13. The composition of claim 12 wherein the polymer matrix component is in the form of porous particles.

14. The composition of claim 9 wherein the polymer matrix component is in the form of porous particles.

15. The composition of claim 12 wherein the osteogenic protein is selected from the group consisting of the members of the BMP-family.

16. The composition of claim 15 wherein the osteogenic protein is BMP-2.

17. The composition of claim 16 wherein the cellulosic material is selected from hydroxypropylmethylcellulose and carboxymethylcellulose.

18. The composition of claim 17, wherein the polymer matrix component is a copolymer of lactic acid and glycolic acid.

19. The composition of claim 18 wherein the polymer matrix component is in the form of porous particles.

20. The composition of claim 17 wherein the polymer matrix component is in the form of porous particles.

21. The composition of claim 16 wherein the polymer matrix component is in the form of porous particles.

22. The composition of claim 15 wherein the cellulosic material is selected from hydroxypropymethylcellulose and carboxymethylcellulose.

23. The composition of claim 22 wherein the polymer matrix component is in the form of porous particles.

24. The composition of claim 12 wherein the osteogenic protein is selected from TGF-$\beta$, Vgr-1, COP-5 and COP-7.

25. The composition of claim 12 wherein the osteogenic protein is OP-1.

26. A composition consisting essentially of a pharmaceutically acceptable admixture of (i) BMP-2;

(ii) a polymeric matrix component comprising polymeric particles having a diameter of between about 150 and 850 microns and a porosity such that the surface area of the particles is between about 0.02 and 4 $m^2/g$, wherein the polymer is selected from the group consisting of poly(lactic acid), poly(glycolic acid), and copolymers of lactic acid and glycolic acid; and (iii) a protein sequestering amount of carboxymethylcellulose.

* * * * *